United States Patent [19]
Bryson, Jr. et al.

[11] Patent Number: 5,148,984
[45] Date of Patent: Sep. 22, 1992

[54] DEVICE FOR DISPENSING A VAPORIZABLE MATERIAL

[75] Inventors: John D. Bryson, Jr., Pewaukee, Wis.; Robert G. Kopp, Algonquin, Ill.

[73] Assignee: Vaportek, Inc., Sussex, Wis.

[21] Appl. No.: 669,075

[22] Filed: Mar. 14, 1991

[51] Int. Cl.$^5$ ............................................. A61L 9/04
[52] U.S. Cl. ........................................ 239/58; 239/55; 239/57
[58] Field of Search ................ 239/36, 55, 57, 58, 239/59, 53, 54, 60; 220/306, 366, 367

[56] References Cited

U.S. PATENT DOCUMENTS

| | | | |
|---|---|---|---|
| 2,555,047 | 5/1951 | Logue | 239/57 |
| 2,836,462 | 5/1958 | Wenner | 239/57 |
| 3,807,082 | 4/1974 | Hautmann et al. | 239/55 |
| 4,014,501 | 3/1977 | Buckenmayer | 220/366 |
| 4,258,004 | 3/1981 | Valenzona et al. | 239/57 |
| 4,279,373 | 7/1981 | Montealegre | 239/57 |
| 4,352,457 | 10/1982 | Weick | 239/57 |
| 4,549,693 | 10/1985 | Barlics | 239/55 |
| 4,733,778 | 3/1988 | Boeckmann et al. | 220/306 |
| 4,917,254 | 4/1990 | Ciriacks | 239/57 |
| 5,004,138 | 4/1991 | Gabas | 239/57 |

Primary Examiner—Andres Kashnikow
Assistant Examiner—Christopher G. Trainor
Attorney, Agent, or Firm—Michael, Best & Friedrich

[57] ABSTRACT

A device for dispensing a vaporizable material including a base adapted to support thereon an air freshener element and adapted to be supported on a pivotable door, a cover supported on the base and cooperating with the base to define an air passage communicating with the air freshener element, guide rails for affording selective movement of the cover relative to the base between a closed position wherein the air passage is substantially obstructed by a baffle and an open position wherein the device promotes passage of a flow of air through the passage during pivotal movement of the door, and detents on the base and cover which cooperate to retain the relative position of the cover and base during pivotal movement of the door.

13 Claims, 2 Drawing Sheets

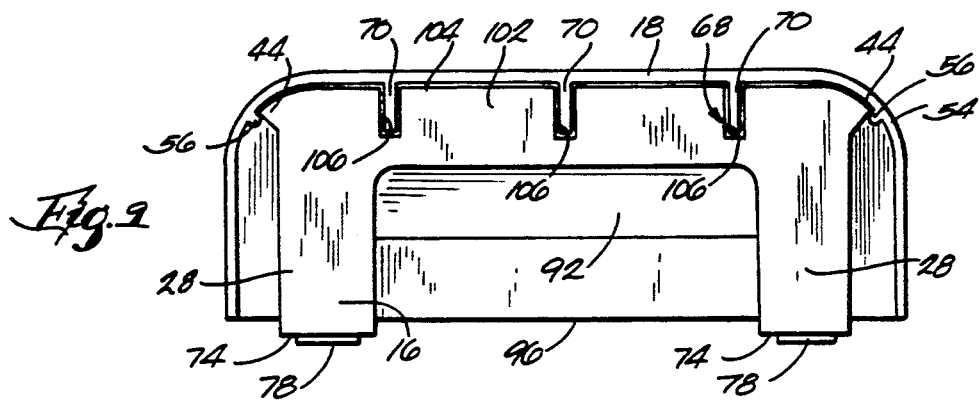
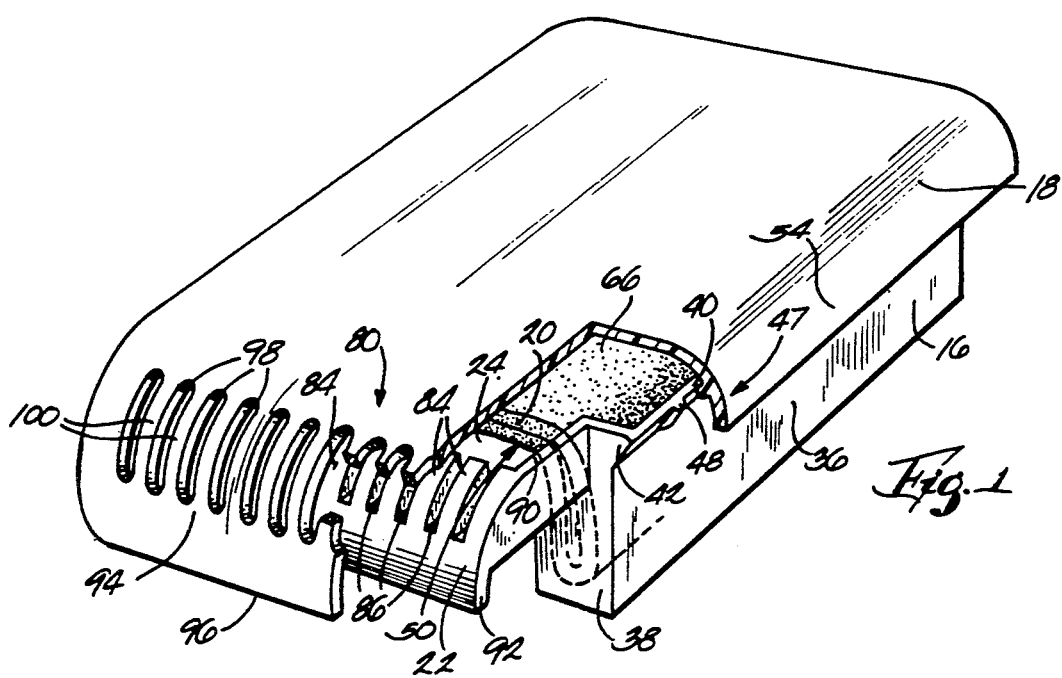

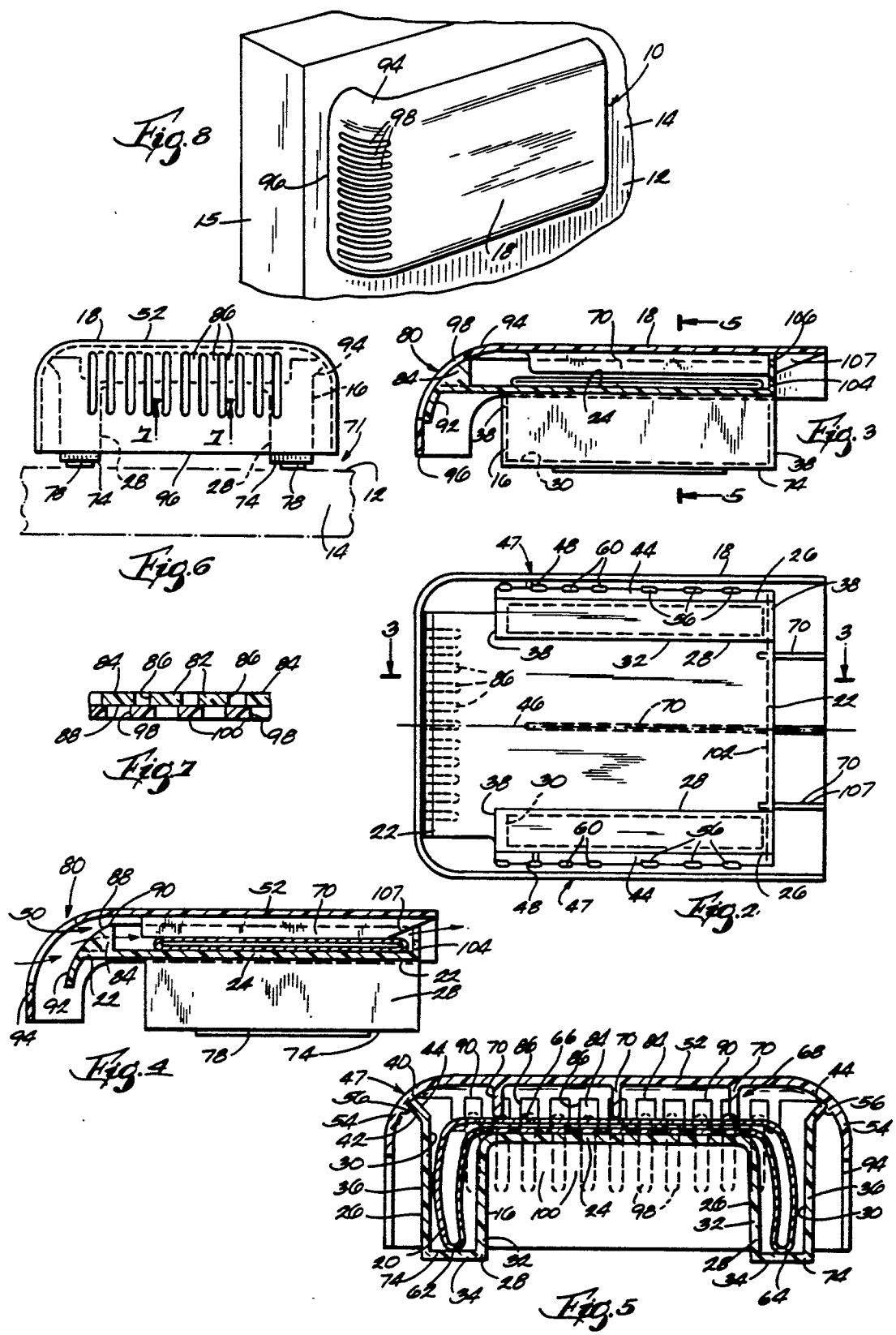

DEVICE FOR DISPENSING A VAPORIZABLE MATERIAL

BACKGROUND OF THE INVENTION

1. Technical Field

The invention relates generally to devices adapted to support a vaporizable material, and more particularly to devices for dispensing a vaporizable material into the ambient air.

2. Relation to Prior Art

Devices adapted to dispense a vaporizable material into the ambient air are known. It is also known to provide such a device with apparatus to support the vaporizable material so that the vaporizable material is exposed to ambient air.

It is also known to provide devices which include a powered fan or which can be waved by hand so that vaporizable material supported by the device is exposed to a flow of air.

SUMMARY OF THE INVENTION

One problem associated with such conventional designs for vapor dispensing devices not including fans and other means for generating a flow of air is that when such dispensers are placed in relatively stagnant ambient air, the vaporizable material is poorly dispensed or is not dispensed at all because of an insufficient flow of air over the vaporizable material.

Another problem associated with known designs for devices to dispense a vaporizable material is that the vaporizable material can vaporize and be spent without being adequately dispensed in the surrounding air.

Accordingly, it is an object of the invention to provide a device which dispenses a vaporizable material in relatively stagnant air without the use of a fan or other powered air flow generator.

It is another object of the invention to provide a device which is adapted to house a vaporizable material and which retards the vaporization of the vaporizable material when the vaporizable material is not dispensed.

In order to achieve these and other objects, the invention provides a device for dispensing a vaporizable material including a base adapted to house an element containing a vaporizable material, such as an air freshener element, and adapted to be mounted on a moveable frame. The device also provides a cover supported on the base and cooperating therewith to define an air passage communicating with the air freshener element. The device also provides dispensing means for dispensing air freshener in response to movement of the frame.

More particularly, the base includes a first air passage surface and the cover includes a second air passage surface. The device also includes support means located on the base and the cover for supporting the cover on the base so that the first and second air passage surfaces are in spaced, opposed relation and define therebetween an air passage communicating with the air freshener element. In one embodiment of the invention, the support means provides means for affording selective movement of the cover relative to the base between a closed position wherein the air passage is substantially obstructed and an open position wherein the air passage affords flow of air therethrough during pivotal movement of the door.

When mounted on a moveable frame, the base and cover cooperate to hold the air freshener in the air passage and movement of the frame, such as the opening and closing of a door, causes a flow of air around the dispenser. The arrangement of the air passage through the device allows a flow of air to pass over the air freshener element to carry vaporized air freshener from the element into the ambient air.

The invention also provides baffle means for selectively opening and closing the air passage. In one embodiment of the invention, the baffle means includes a row of finger-like members extending into the air passage and a slotted portion of the cover moveable relative to the row of fingers so that the fingers and slots are moveable between an open position and a closed position wherein the air passage is substantially obstructed.

The baffle means affords control over the amount of air allowed to flow over the element. The baffle means also serves to retard the vaporization of the air freshener from the element by providing means to close the air passage to prevent the escape therefrom of vaporized air freshener.

A principal feature of the invention is the provision of an air freshener dispenser which utilizes the movement of air caused by the opening and closing of a door to dispense the fragrance of a liquid-filled semi-permeable membrane air freshening element.

Another principal feature of the invention is the provision of an air freshener dispenser which does not require electricity or batteries to dispense an air freshener.

Another principal feature of the invention is the provision of a door mounted air freshener dispenser which includes a means for adjusting the amount of fragrance which is dispensed when the door is pivoted.

Various other features and advantages of the invention will become apparent to those skilled in the art upon review of the following detailed description, claims and drawings.

DESCRIPTION OF THE DRAWINGS

FIG. 1 is a perspective view, partially broken away for illustration, of a device embodying the invention.

FIG. 2 is a bottom plan view of the dispenser illustrated in FIG. 1.

FIG. 3 is a cross-sectional view taken along line 3—3 in FIG. 2 illustrating the dispenser in the closed position.

FIG. 4 is a view similar to FIG. 3 illustrating the dispenser in the open position.

FIG. 5 is a cross-sectional view taken along 5—5 in FIG. 3.

FIG. 6 is elevational end view of the dispenser illustrated in FIG. 1.

FIG. 7 is a view taken along line 7—7 in FIG. 6.

FIG. 8 is a perspective view of the dispenser illustrated in FIG. 1 mounted on a vertical surface of a moveable frame.

FIG. 9 is an elevational view of the end of the dispenser opposite to that illustrated in FIG. 6.

Before one embodiment of the invention is explained in detail, it is to be understood that the invention is not limited in its application to the details of construction and the arrangement of components set forth in the following description or illustrated in the drawings. The invention is capable of other embodiments and of being practiced or being carried out in various ways. Also, it is to be understood that the phraseology and terminology used herein is for the purpose of description and should not be regarded as limiting.

DETAILED DESCRIPTION

The drawings illustrate a device 10 for dispensing a vaporizable material into the surrounding ambient air. The dispensing device 10 can be used to dispense a wide variety of vaporizable solid and liquid materials including odorants, deodorants, insecticides, repellants and attractants. The device 10 is particularly well-suited for use as an air freshener or odor control compound dispenser, however, and the following detailed description, as well as the drawings, describe the device 10 in terms of that particular application. The device 10 is adapted to be mounted on a support surface 12 provided by a support member or some other frame 14 such as a pivotable door 15 which is moveable through the ambient air. For example, FIG. 8 illustrates the device 10 fixed to a vertically extending support surface 12 provided by the side of a door 15. However, the device 10 can also be fixed to support surfaces which extend in other directions. The device 10 does not include powered means for dispensing the vaporizable material. Rather, device 10 utilizes air flows created by movement of the support frame 14 to promote a flow of air to pass over and disperse the vaporizable material.

The device 10 includes (FIG. 1) a base 16, a cover 18 which is supported on the base 16 and an air freshener element or odor control element 20 housed by the base 16 and cover 18. The base 16 (FIGS. 3, 4) has opposite ends 22, a generally flat central portion 24 and (FIG. 5) a pair of spaced-apart side portions 26 connected with the central portion 24. The side portions 26 are in the form of support legs 28 which give the base 16 a generally inverted U-shape when viewed from either opposite end and which each define a retainer cavity 30 adapted to house a portion of the air freshener element 20. The retainer cavities 30 are located adjacent the central portion 24 and extend between the opposite ends 22 of the base 16. The cavities 30 are defined by (FIG. 5) an inner sidewall 32 which extends generally perpendicularly to the central portion 24 and a mounting wall 34 which is connected to, and extends perpendicularly between the inner sidewall 32 and an outer sidewall 36. Two pairs of end walls 38 extend between the inner and outer sidewalls 36 and the mounting walls 34 to close the ends of the support legs 28 so that the cavities 30 open toward the cover 18 and so that, when the device 10 is mounted on the support surface 12, the cavities 30 open away from the support surface 12.

The outer sidewalls 36 of the support legs 28 are generally parallel to the inner sidewalls 32 and extend from the mounting walls 34 toward and beyond the central portion 24 of the base 16. The outer sidewalls 36 terminate in a free edge 40 including a laterally, outwardly splayed portion 42. The outwardly splayed portions 42 of the outer walls provide guide rails 44 which slideably engage the cover 18 to support the cover 18 on the base 16. The guide rails 44 are (FIG. 2) parallel to the longitudinal axis 46 of the base 16 and provide means 47 along which the cover 18 can be moved relative to the base 16. Each guide rail 44 has (FIGS. 1, 2) an outwardly extending projection or detent 48 which is engageable with the cover 18 to secure the cover 18 in position relative to the base 16 in a manner discussed below.

The cover 18 is supported on the base 16 by the guide rails 44 so as to house the air freshener element 20 and cooperates with the base 16 to define (FIGS. 1, 4) an air passage 50 extending between the opposite ends 22 of the base 16 and communicating with the air freshener element 20. More particularly, the cover 18 includes a generally flat central portion 52 and (FIG. 5) a pair of rounded sidewalls 54 which extend from the flat portion 52 and generally wrap around the outer sidewalls 36 of the base 16. When the cover 18 is placed on the base 16, the central portion 52 of the cover 18 is in opposed, spaced relation to the central portion 24 of the base 16. The air passage 50 defined by the cover 18 and the base 16 extends (FIGS. 3, 4) between the opposite ends 22 of the base 16 and (FIG. 5) between the respective side portions 54, 26 of the cover 18 and the base 16 and the respective central portions 52, 24 of the cover 18 and the base 16.

The cover 18 includes (FIGS. 1,2) a plurality of inwardly extending, longitudinally spaced projections or guides stops 56 which are disposed on the concave surfaces of the rounded sidewalls 54. The guides 56 (FIG. 2) are aligned parallel to the axis 46 on each of the rounded sidewalls 54 to form a row of guides 56 for slidingly engaging a respective guide rail 44 and cooperating therewith to guide longitudinal movement of the cover 18 relative to the base 16 along the axis 46. The guide 56 extends inwardly a small distance over the edges 40 of the rails 44 to retain the cover 18 on the base 16.

The cover 18 also includes a plurality of longitudinally spaced position stops 60 which are relatively closely- spaced and which are in the row of guides 56. The position stops 60 are arranged to engage the detents 48 located on the guide rails 44 and cooperate therewith to provide means for selectively retaining the cover 18 in various positions relative to the base 16 along the axis 46. Engagement between the position stops 60 and the detents 48 also provides means for retaining the position of the base 16 relative to the cover 18 during pivotal movement of the frame 14.

The air freshener or odor control element 20 comprises a relatively thin, flexible membrane which is impregnated with an aromatic, vaporizable air freshener. In the preferred embodiment illustrated, the air freshener element 20 is a sealed, flexible package or envelop made from a gas-permeable, thermoplastic material such as polyethelene film and containing a vaporizable odor control compound. Suitable liquid odor control compounds are sold by Vaportek, Inc., Sussex, Wis. and are identified by Vaportek catalog Nos. 90-9910 and 90-9911. The liquid compound can vaporize at room temperature and atmospheric pressure so that the liquid can permeate through the wall of the envelop. While various suitable constructions of the air freshener element 20 can be used, U.S. Pat. No. 3,785,556 which issued to Watkins on Jan. 15, 1974 discloses a preferred construction for the air freshener element 20 and is incorporated herein by reference.

As best shown in FIG. 5, the element 20 has a portion 62 which is housed by one of the retainer cavities 30, a portion 64 housed in the other of the retainer cavities 30 and an intermediate portion 66 which extends between the retainer cavities 30 across the central portion 24 of the base 16. The intermediate portion 66 of the element 20 is held in position against the central portion of the cover 18 by spacer means 68 for maintaining a space between the element 20 and the inner surface of the cover 18. While other suitable spacer means can be used, in the specific embodiment illustrated, the spacer means 68 includes (FIGS. 3 and 5) one or more spacer ribs 70 or members which extend from the inner surface of the cover 18 and engages the element 20 to maintain a space between the element 20 and the central portion of the cover 18. The spacer ribs 70 also substantially prevent contact between the cover 18 and the element 20. Any suitable number of spacer ribs 70 can be provided. In the illustrated embodiment, the spacer means 68 comprises three elongated spacer ribs 70 which extend generally parallel to the axis 46; a central one of the spacer ribs 70 extending substantially the entire length of the air passage 50, and a pair of lateral spacer ribs 70 disposed on either side of the central spacer rib 70.

The device 10 also includes (FIG. 6) means 71 for mounting the device 10 on the support surface 12 of the moveable frame 14. Particularly, the mounting walls 34 of each support leg 28 provide a mounting surface 74 which supports mounting means for fastening the base 16 to a support surface 12. The illustrated mounting means is in the form of two-sided adhesive pads 78 (FIG. 6), each of which have a first adhesive side attached to a mounting surface 74 and a second adhesive side covered by paper (not shown) that can be removed to securely fasten the base 16 to the support surface 12. When mounted on such a support surface 12 by the mounting means 71 provided on the support legs 28, the central portion 24 of the base 16 and the cover 18 are substantially parallel to, and face away from, the support surface 12. Also when the device 10 is mounted on a vertical support surface 12, the spacer means 68 retains the element 20 in position against the central portion 24 of the base 16 and maintains a sufficient clearance between the cover 18 and the element 20 to provide a substantially unobstructed flow path over the element 20.

The device 10 also includes (FIGS. 1, 7) baffle means 80 for selectively and adjustably opening and closing the air passage 50. While various constructions for the baffle means 80 could be used, in the preferred embodiment, the baffle means 80 includes (FIGS. 1, 3) a plurality of members or fingers 84 disposed on the base 16 which extend into the air passage 50. The fingers 84 are substantially uniformly-spaced and are arranged in a row extending between the side portions 26 of the base 16 and are located adjacent one of the opposite ends 22 of the base 16. The fingers 84 define therebetween (FIGS. 1, 7) a plurality of interdigital spaces 86 and each have a forward facing surface 88 which curves away from the central portion 24 of the base 16 and toward the cover 18. The ends 90 of the fingers 84 are (FIG. 5) closely spaced to the cover 18 and are substantially flush with the free edge 40 of the guide rails 44. The baffle means 80 also includes a laterally extending air dam 92 which is located adjacent the row of fingers 84 and which curves away from the central portion 24 of the base 16 so as to continue the curved contour of the row of fingers 84. Together the row of fingers 84 and the air dam 92 form a curved portion which is engageable with the cover 18.

The baffle means 80 also includes a baffle portion 94 of the cover 18 which can be moved relative to the row of fingers 84 between (FIG. 4) an open position wherein the baffle portion 94 and row of fingers 84 are spaced apart so that air passage 50 is open and (FIG. 3) a closed position wherein the row of teeth and the baffle portion 94 of the cover 18 are closely spaced and the air passage 50 is substantially obstructed. As shown in FIGS. 1 and 6, the baffle portion 94 of the cover 18 extends from the generally flat portion of the cover 18 and substantially surrounds the curved portion of the base 16. The baffle portion 94 has a generally curved profile (when viewed perpendicular to axis 46) which is similar to the convex contour defined by the curved portion of the base 16 and has a leading edge 96 which extends beyond the edge of the air dam. When the device 10 in mounted on a support surface 12, the leading edge 96 of the baffle portion 94 is relatively closely spaced to the support surface 12.

The baffle portion 94 of the cover 18 also has a plurality of elongated, relatively thin slots 98 which define therebetween a plurality of generally elongated laths 100. Each of the slots 98 (FIGS. 1 or 7) is communicable with the air passage 50, is respectively registered with one of the fingers 84 and has a width which is approximately equal to the width of the fingers 84. Similarly, each of the plurality of laths 100 is registered with one of the interdigital spaces 86 defined by the fingers 84 and has a width which is approximately equal to the width of the one of the spaces 86.

The baffle means 80 also includes (FIGS. 2, 9) a trailing edge wall 102 which is located at end 22 of the base 16 opposite the fingers 84, which extends laterally between the outer sidewalls 36 and which has (FIG. 9) a free edge 104 substantially flush with free edge 40 of the guide rails 44 and closely spaced to the cover 18. The trailing edge wall 102 has therein a plurality of guide slots 106 which open to the free edge 104 of the trailing edge wall 102 and which are spaced-apart across the length of the trailing edge wall 102. The number of guide slots 106 provided should correspond to the number of spacer ribs 70 provided on the cover 18. Accordingly, the illustrated trailing edge wall 102 has three guide slots 106. As shown in FIG. 9, each guide slot 106 is located so as to register with one of the spacer ribs 70 so as to provide free sliding movement of the cover 18 relative to the base 16 without interference with the trailing edge wall 102.

The baffle means 80 also includes means for affording selective movement of the fingers 84 relative to the slots 98 and for opening and closing the air passage 50. While various other constructions could be employed in the illustrated embodiment, the means for affording movement of the fingers 84 relative to the slots 98 includes the cooperating, sliding engagement of the guide stops 56 and guide rails 44 for affording movement of the cover 18 relative to the base 16 along the axis 46 between the first or closed position (FIGS. 3, 7) wherein the row of fingers 84 and the baffle portion 94 are relatively closely-spaced and the second or open position (FIG. 4) wherein the row of fingers 84 and the baffle portion 94 are spaced-apart. Preferably, the detents 48 on the guide rails 44 and the position stops on the cover 18 are arranged to selectively retain the cover 18 in the open and closed positions, as well as positions intermediate the open and closed position.

The baffle means 80 thus also provides means for moving the spacer ribs 70 relative to the guide slots 106 so as to alternatingly obstruct and open the guide slots 106. When the cover 18 is in the closed position (FIG. 3), the spacer ribs 70 are received by the guide slots 106 and substantially obstruct the guide slots 106 to prevent a flow of air therethrough. The trailing end 107 of the spacer ribs 70 preferably taper toward the inner surface of the cover 18 so that when the cover 18 is moved relative to the base 16 from the closed position (FIG. 3) to the open position (FIG. 4), the tapered portions 107 of the spacer ribs 70 are disposed in the guide slots 106 to afford a flow of air through the space between the tapered portions 107 and the guide slots 106.

Movement of the frame 14 through the ambient air, such as opening and closing of the door 15, causes air pressure differentials which result in flows of air around the frame 14 and the device 10. As a result of such pivotal movement, a flow of air enters an end of the device 10 and passes through the air passage 50 and over the element 20. Vaporized oderant from the element 20 is carried by the flow through the device 10 and is dispensed into the ambient air.

More particularly, when the cover 18 is moved into the open position, pivotal movement of the frame 14 causes a flow of air to pass through the baffle portion 94 of the cover 18, through the row of fingers 84, across the element 20 and withdraws the odorant in vapor form therefrom. The flow of air continues across the element 20 and out of the air passage 50 by way of the opened guide slots 106 in the trailing edge wall 102. Thus, the dispenser comprises means for dispensing air freshener in response to pivotal movement of the door 15 and includes means for promoting a flow of air through the air passage 50 during movement of the frame 14.

When mounted in such a manner on a moveable frame 14, the cover 18 can still be moved relative to the base 16 and, by virtue of the detents 48 on the base 16, can be retained in a selected position during pivotal movement of the frame 14. The capacity for multiple positioning of the cover 18 on the base 16 provides means for adjusting the amount of air flow through the dispenser and thus also provides means for adjusting the amount of air freshner dispensed in response to movement of the door 15.

When the cover 18 is in the closed position (FIGS. 3 and 7), the curved portion of the base 16 engages the baffle portion 94 of the cover 18 so that the fingers 84 and the slots 98 are closely spaced and substantially obstruct the air passage 50. Also, the air passage 50 is obstructed by the housed relationship of the spacer ribs 70 and guide slots 106 and by the close spacing of the trialing edge wall and cover 18. When in the open position (FIG. 4) the fingers 84 and the slots 98 are spaced-apart so that a flow of air can pass through the slots 98, through the interdigital openings, and into the air passage 50. Also, the tapered portions 107 of the spacer ribs 70 move into registry with the guide slots 106 and affords passage therethrough of a flow of air.

Also, when in the closed position, the baffle means 80 prevents the flow of air through the air passage 50 and retards the escape of odor control vapor from the dispenser, thereby prolonging the effective lifetime of the element 20.

Various other features of the invention are set forth in the following claims:

1. A device for dispensing a vaporizable material comprising a base adapted to be mounted on a moveable frame, a cover cooperating with said base to define therebetween an air passage having a first end and a second end spaced from said first end, an element containing vaporizable material disposed in said air passage, means for supporting said cover on said base for rectilinear movement relative to said base and in the direction of the spacing of said ends of said air passage, and means for dispensing the vaporizable material in response to movement of the frame, said dispensing means including means at one of said ends of said air passageway and on one of said base and said cover for selectively and adjustably opening and closing said air passage to afford air passage through said ends of said air passage in response to rectilinear movement of said cover relative to said base.

2. A device for dispensing a vaporizable material as set forth in claim 1 wherein said base has a first surface, wherein said cover has a second surface which is in opposed spaced relation to said first surface, and wherein said first and second surface define said air passage.

3. A device for dispensing a vaporizable material as set forth in claim 1 wherein said cover includes spacing means for maintaining a space between said element and said cover.

4. A device for dispensing a vaporizable material as set forth in claim 3 wherein said base has a first surface, wherein said element is supported by said base adjacent said first surface, and wherein said spacing means includes a member disposed on said cover and which extends generally toward said first surface.

5. A device for dispensing a vaporizable material comprising a base adapted to be mounted on a moveable frame, a cover cooperating with said base to define therebetween an air passage, an element containing vaporizable material disposed in said air passage, means for supporting said cover on said base for rectilinear movement relative to said base, and means for dispensing the vaporizable material in response to movement of the frame, said dispensing means including means on said base and on said cover for selectively and adjustably opening and closing said air passage in response to rectilinear movement of said cover relative to said base, said means for opening and closing said air passage including, on one of said base and said cover, a plurality of fingers extending into said air passage, and on the other of said base and said cover, a portion which has therethrough a plurality of spaced-apart slots communicable with said air passage and respectively registered with said plurality of fingers, and wherein rectilinear movement of said cover affords movement of said fingers relative to said slots between an open position wherein said fingers are spaced from said slots and a closed position wherein said fingers and said slots are closely spaced to substantially obstruct said air passage.

6. A device for dispensing a vaporizable material as set forth in claim 5 wherein said base has a first portion having a curved contour, wherein said cover has a second portion having a contour corresponding to said curved contour, and wherein said first and second curved portions engage when the cover is moved into said closed position.

7. A device for dispensing a vaporizable material as set forth in claim 6 wherein said base includes a pair of generally parallel rails, and wherein said cover includes means for slidably engaging with said rails.

8. A device for dispensing a vaporizable material as set forth in claim 7 wherein said means for supporting said cover on said base includes means for retaining said cover in a selected position relative to said base during movement of the frame.

9. A device for dispensing a vaporizable material comprising a base adapted to be supported on a pivotable door, said base including a first air passage surface, a cover including a second air passage surface, and support means for supporting said cover on said base so that said first and second air passage surfaces are in spaced, opposed relation and define therebetween an air passage, an element containing vaporizable material disposed in said air passage, said air passage having a first end and a second end spaced from said first end, said support means including means for affording selective rectilinear movement of said cover relative to said base and in the direction of the spacing of said ends of said air passage and between a closed position and a spaced opened position, said cover and said base including cooperating means located adjacent one of said ends of said air passage and operable, when said cover is in said closed position, to substantially obstruct said air passage and, when said cover is in said opened position, to afford flow of air through said ends of said air passage during pivotal movement of the door.

10. A device for dispensing a vaporizable material comprising a base adapted to be supported on a pivotable door, said base including a first air passage surface, a cover including a second air passage surface, and support means for supporting said cover on said base so that said first and second air passage surfaces are in spaced, opposed relation and define therebetween an air passage an element containing vaporizable material disposed in said air passage, said support means including means for affording selective rectilinear movement of said cover relative to said base between a closed position and a spaced opened position, said cover and said base including cooperating means operable, when said cover is in said closed position, to substantially obstruct said air passage and, when said cover is in said opened position, to afford flow of air through said air passage during pivotal movement of the door, said cooperating means on said cover and said base including a plurality of members which are located on one of said base and said cover, which extend into said air passage, and which define therebetween a plurality of generally elongated slots communicable with said air passage, said members and said slots being selectively movable relative to each other between said closed position wherein said members substantially obstruct said slots and said open position wherein said members are spaced from said slots.

11. A device for dispensing a vaporizable material comprising a base adapted to be mounted on a moveable frame, a cover supported by said base, defining with said base an air passage located therebetween, an element containing vaporizable material disposed in said air passage, said air passage, having a first end and a second end spaced from said first end, said cover being movable rectilinearly in the direction of the spacing of said ends of said passage and with respect to said base between opened and closed positions, and cooperating means at one of said ends of said air passage and on one of said cover and said base for selectively opening and closing said air passage to afford air passage through said ends of said air passage in response to rectilinear movement of said cover between said opened and closed positions.

12. A device for dispensing a vaporizable material as set forth in claim 11 wherein said base includes a first air passage surface, wherein said cover includes a second air passage surface which is in opposed spaced relation to said first air passage surface, and wherein said first and second air passage surfaces define said air passage.

13. A device for dispensing a vaporizable material comprising a base which is adapted to be mounted on a movable frame and which includes a first air passage surface, a cover supported by said base and including a second air passage surface and which is in opposed spaced relation to said first air passage surface which defines with said first air passage surface an air passage an element containing vaporizable material disposed in said air passage, said cover being movable rectilinearly with respect to said base between opened and closed positions, and cooperating means on said cover and on said base for selectively opening and closing said air passage in response to rectilinear movement of said cover between said opened and closed positions at least one member located on one of said base and said cover and extending into said air passage, at least one opening which is located in a portion of the other of said base and said cover, which is communicable with said air passage, and which is registered with said member, said member and said opening being spaced from each other when said cover is in said opened position and said member being adjacent said opening when said cover is in said closed position so as to substantially obstruct said air passage.

* * * * *